United States Patent [19]
Larkin et al.

[11] Patent Number: 6,063,145
[45] Date of Patent: May 16, 2000

[54] FUEL COMPOSITIONS CONTAINING ETHERAMINE ALKOXYLATES

[75] Inventors: John M. Larkin; Wei-Yang Su; Terry L. Renken, all of Austin, Tex.

[73] Assignee: Huntsman Petrochemical Corporation, Austin, Tex.

[21] Appl. No.: 09/105,773

[22] Filed: Jun. 26, 1998

Related U.S. Application Data

[60] Provisional application No. 60/051,099, Jun. 27, 1997.

[51] Int. Cl.⁷ .............................. C10L 1/22; C07C 217/00
[52] U.S. Cl. .............................. 44/434; 44/424; 564/346; 564/347; 564/348
[58] Field of Search ........................................ 44/424, 434

[56] References Cited

U.S. PATENT DOCUMENTS

| | | | |
|---|---|---|---|
| 3,705,024 | 12/1972 | Zimmerman et al. | 44/432 |
| 4,391,610 | 7/1983 | Sung et al. | 44/434 |
| 4,409,000 | 10/1983 | LeSuer | 44/434 |
| 4,460,379 | 7/1984 | Sweeney et al. | 44/434 |
| 5,112,364 | 5/1992 | Rath et al. | 44/418 |
| 5,616,811 | 4/1997 | Vipond et al. | 564/505 |

FOREIGN PATENT DOCUMENTS

| | | |
|---|---|---|
| 0 356 725 | 7/1989 | European Pat. Off. . |
| 2 402 473 | 4/1979 | France . |
| WO 97/30103 | 8/1997 | WIPO . |

OTHER PUBLICATIONS

International Search Report dated Oct. 28, 1998.

*Primary Examiner*—Ellen M. McAvoy
*Attorney, Agent, or Firm*—O'Keefe, Egan and Peterman

[57] ABSTRACT

This invention concerns a fuel additive comprising an etheramine alkoxylate, and fuel compositions and additive concentrates made therefrom. The etheramine alkoxylate may be of formula:

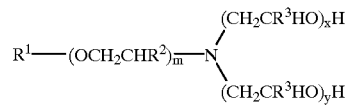

where $R^1$ is a straight or branched alkyl, or alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

19 Claims, No Drawings

FUEL COMPOSITIONS CONTAINING ETHERAMINE ALKOXYLATES

This application claims priority from provisional application Ser. No. 60/051,099, filed Jun. 27, 1997.

BACKGROUND OF INVENTION

This invention concerns a fuel composition containing a petroleum fuel and a etheramine alkoxylate.

Petroleum distillates have long been used as fuels for internal combustion engines. In recent years, research has been directed toward preparing fuel compositions containing additive which acts as a surface-active agent for improving fuel distribution to prevent poor driving performance due to the maldistribution of fuel-air mixture between the cylinders. New and usefuil fuel compositions having this kind of components are highly desirable.

SUMMARY OF INVENTION

This invention is a novel fuel composition, which provides a solution to the problems, needs, and disadvantages described above.

In one broad respect, this invention is a fuel additive, comprising: an etheramine alkoxylate of formula:

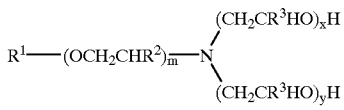

where $R^1$ is a straight or branched alkyl or alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

In another broad respect, this invention is a fuel composition, comprising: a petroleum fuel and an etheramine alkoxylate of formula:

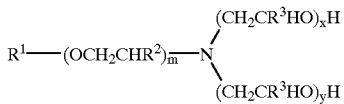

where $R^1$ is a straight or branched alkyl or alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

In yet another broad respect, this invention is a fuel additive concentrate comprising from about 10 parts to about 2000 parts etheramine alkoxylate, with the balance comprising a petroleum distillate fuel, wherein the etheramine alkoxylate is of formula:

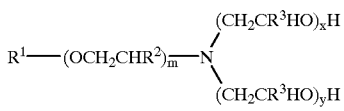

where $R^1$ is a straight or branched alkyl, or alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4. In this embodiment, the concentrate may contain from about 30 to about 400 parts of etheramine alkoxylate.

In certain embodiments of this invention, $R^1$ is alkyl of from 8 to 24 carbon atoms, or $R^1$ is alkylaryl and contains from about 7 to about 30 carbon atoms, or $R^1$ is alkylaryl and the alkylaryl is disubstituted with alkyl groups, or $R^2$ contains 1 or 2 carbon atoms, or $R^2$ is hydrogen, or $R^3$ is hydrogen, or $R^3$ is alkyl containing 1 or 2 carbons, or x+y ranges from about 1 to about 3, or wherein the etheramine alkoxylate is present in an amount effective to provide fuel distribution properties of the composition.

The compositions of this invention are useful as fuel additives and as fuel compositions for internal combustion engines and the like.

DETAILED DESCRIPTION OF THE INVENTION

The starting materials for preparing the etheramine alkyloxylates of this invention may be an alkoxylated alcohol or phenol of the formula, $R^1-(OCH_2CHR^2)_m-OH$, wherein $R^1$, $R^2$ and m are as described herein. The starting materials may be prepared by known methods, such as by alkoxylation of alcohols and phenols with alkylene oxide in the presence of an alkoxylation catalyst such as NaOH or KOH.

The alkoxylated alcohol or phenol is reacted with ammonia using known techniques, such as by reaction with ammonia in the presence of an amination catalyst to produce an etheramine. The anination step typically is conducted at a temperature in the range from about 100 to about 300 degrees Centigrade, preferably from about 190 to about 220 degrees Centigrade. The pressure is typically maintained in the range from about 500 to about 5000 psi. One such amination procedure is described in U.S. Pat. No. 5,616,811.

The etheramine is next alkoxylated with an alkylene oxide using conventional techniques to produce etheramine alkoxylates. Representative examples of such alkylene oxides include ethylene oxide, propylene oxide, 1, 2-butylene oxide, 2, 3-butylene oxide or mixtures thereof. In certain embodiments, the alkylene oxides are ethylene oxide, propylene oxide or mixture thereof. Ethylene oxide is the preferred alkylene oxide.

The fuel compositions of this invention include an etheramine alkoxylate as described above in combination with a petroleum fuel. Representative examples of such petroleum distillate fuels include, but are not limited to, gasoline, diesel, and the like. The concentration of etheramine alkoxylate may vary depending on a wide variety of factors such as presence of detergents, dispersants, and other additives; and the like. Generally, the etheramine alkoxylate is present in an amount effective to provide fuel distribution properties of the composition. For example, the etheramine alkoxylate may be employed in a concentration of from about 10 parts per million to about 5000 parts per million.

The etheramine alkoxylate may be formulated as a concentrate, using a petroleum distillate as the base stock.

In gasoline fuels, other fuel additives may also be included such as antiknock agents such as methylcyclopentadienyl manganese tricarbonyl, tetramethyl, or tetraethyl lead, or other dispersants or detergents such as various substituted succinimides, amines, etc.

The fuel compositions of this invention may be readily prepared by, for example, dispersing an etheramine alkoxylate in a selected petroleum distillate fuel as by adding the etheramine alkoxylate to a petroleum distillate and stirring or otherwise agitating the resulting solution to evenly disperse the etheramine alkoxylate in the composition. In this regard, any of the conventional methods of blending fuels may be employed.

The following examples are illustrative of the invention, but are not intended to limit the scope of the invention or claims thereof. Unless otherwise denoted, all percentages are by weight. In the examples, "meq/g" means milliequivalents per gram. Also, an EPALT™ alcohol is an linear primary alcohol.

EXAMPLE 1

General Procedure for the Preparation of Etheramine Alkoxylate

About 48.04 lbs of an aminated 3.0-mole ethylene oxide adduct of EPAL™ 1214 alcohol was charged into a reactor. The etheramine was dried to <0.05% of water via nitrogen purge at 130° C. Ethylene oxide (10.96 lbs) was added at 140–150° C. and maximum pressure of 50 psig.

The reactor was digested to less than 1 psig pressure drop in 60 minutes. The reactor was then purged for 15 minutes, and product was collected and analyzed. The analysis of this product which is hydrocarbon soluble is as follows: Total Amine, 1.961 meq/g; Tertiary Amine 1.942 meq/g.

EXAMPLE 2

The procedure of Example 1 was followed except that 54.82 lbs of an aminated 2.2-mole propylene oxide adduct of EPAL™ 1214 alcohol and 15.18 lbs of ethylene oxide were used. The analysis of this product which is hydrocarbon soluble is as follows: Total Amine, 2.356 meq/g;

Tertiary Amine, 2.347 meq/g.

EXAMPLE 3

The procedure of Example 1 was followed except that 44.98 lbs of an aminated 3.0-mole propylene oxide adduct of EPAL™ 1618 alcohol and 0.42 lbs of ethylene oxide were used. The analysis of this product which is hydrocarbon soluble is as follows: Total Amine, 1.889 meq/g, Tertiary Amine, 1.872 meq/g.

EXAMPLE 4

The procedure of Example 1 was followed except that 50.55 lbs of aminated 3.0-mole ethylene oxide adduct of EPAL™ 1618 alcohol and 9.45 lbs of ethylene oxide were used. The analysis of this product which is hydrocarbon soluble is as follows: Total Amine, 1.706 meq/g;

Tertiary Amine, 1.704 meq/g.

What is claimed is:

1. An etheramine alkoxylate of formula:

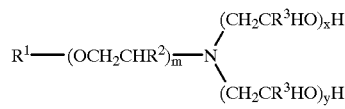

where $R^1$ is an alkylaryl; $R^2$ is independently in each occurrence alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

2. The composition of claim 1 wherein $R^1$ is alkylaryl and contains from about 7 to about 30 carbon atoms.

3. The composition of claim 1 wherein $R^1$ is alkylaryl and the alkylaryl is disubstituted with alkyl groups.

4. The composition of claim 1 wherein $R^2$ contains 1 or 2 carbon atoms.

5. The composition of claim 1 wherein $R^3$ is hydrogen.

6. The composition of claim 1 wherein $R^3$ is alkyl containing 1 or 2 carbons.

7. The composition of claim 1 wherein x+y ranges from about 1 to about 3.

8. A fuel composition, comprising: a petroleum fuel and a etheramine alkoxylate of formula:

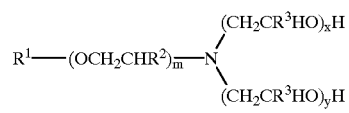

where $R^1$ is an alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

9. The composition of claim 8 wherein $R^1$ is alkylaryl and contains from about 7 to about 30 carbon atoms.

10. The composition of claim 8 wherein $R^1$ is alkylaryl and the alkylaryl is disubstituted with alkyl groups.

11. The composition of claim 8 wherein $R^2$ contains 1 or 2 carbon atoms.

12. The composition of claim 8 wherein $R^2$ is hydrogen.

13. The composition of claim 8 wherein $R^3$ is hydrogen.

14. The composition of claim 8 wherein $R^3$ is alkyl containing 1 or 2 carbons.

15. The composition of claim 8 wherein the petroleum fuel is diesel or gasoline.

16. The composition of claim 8 wherein x+y ranges from about 1 to about 3.

17. The composition of claim 8 wherein the etheramine alkoxylate is present in an amount in the range from about 10 parts per million to about 5000 parts per million based on the total weight of the composition.

18. A fuel additive concentrate comprising from about 10 parts to about 2000 parts etheramine alkoxylate, with the balance comprising a petroleum distillate fuel, wherein the etheramine alkoxylate is of formula:

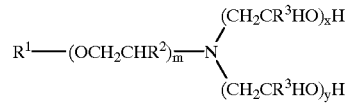

where $R^1$ is an alkylaryl; $R^2$ is independently in each occurrence hydrogen or alkyl from 1 to 6 carbons; $R^3$ is independently in each occurrence hydrogen or alkyl of from 1 to 6 carbons; m averages from about 2 to about 20; and x and y each independently average from about 0 to 2, where x+y averages from about 1 to about 4.

19. The concentrate of claim 16 containing from about 30 to about 400 parts of etheramine alkoxylate.

* * * * *